(12) United States Patent
Moua et al.

(10) Patent No.: US 8,945,122 B2
(45) Date of Patent: Feb. 3, 2015

(54) POWER GLOVE

(75) Inventors: Tony Moua, Broomfield, CO (US); Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 1115 days.

(21) Appl. No.: 12/947,379

(22) Filed: Nov. 16, 2010

(65) Prior Publication Data

US 2012/0123405 A1    May 17, 2012

(51) Int. Cl.
*A61B 18/12* (2006.01)
*A61B 18/10* (2006.01)
*A61B 19/04* (2006.01)
*A61B 18/14* (2006.01)
*A61B 18/00* (2006.01)

(52) U.S. Cl.
CPC ............... *A61B 18/12* (2013.01); *A61B 19/04* (2013.01); *A61B 18/1233* (2013.01); *A61B 18/1402* (2013.01); *A61B 18/1445* (2013.01); *A61B 2018/00922* (2013.01)
USPC .............................................. 606/45; 606/49

(58) Field of Classification Search
USPC .................................................... 606/41, 45
See application file for complete search history.

(56) References Cited

U.S. PATENT DOCUMENTS

| 6,159,200 | A | 12/2000 | Verdura et al. |
| 6,165,184 | A | 12/2000 | Verdura et al. |
| 6,500,169 | B1* | 12/2002 | Deng ................................ 606/1 |
| 6,551,312 | B2 | 4/2003 | Zhang et al. |
| 7,317,955 | B2 | 1/2008 | McGreevy |
| 2002/0128646 | A1* | 9/2002 | Zhang et al. .................... 606/41 |
| 2004/0260281 | A1* | 12/2004 | Baxter et al. .................... 606/41 |
| 2007/0060919 | A1 | 3/2007 | Isaacson et al. |

OTHER PUBLICATIONS

U.S. Appl. No. 12/947,420, filed Nov. 16, 2010, Jason L. Craig.
U.S. Appl. No. 12/947,352, filed Nov. 16, 2010, Jason L. Craig.

\* cited by examiner

*Primary Examiner* — Jaymi Della

(57) ABSTRACT

A system and method for powering a wireless electrosurgical device using a powered glove. The powered glove includes at least a conductive pad on a finger and a thumb. The glove is connected to a generator and supplies power to the wireless electrosurgical device when at least two conductive pads touch conductive buttons on the wireless device. The user selects the operating mode by selecting different combination of conductive buttons and/or switches on the wireless device. The generator senses a voltage drop across a circuit within the electrosurgical device to determine the operating mode. The generator then supplies the RF energy based on the selected operating mode via the glove to the wireless device.

18 Claims, 8 Drawing Sheets

POWER GLOVE

BACKGROUND

1. Technical Field

The present disclosure relates to apparatuses and method for supplying energy to a surgical device, and more particularly, to a power glove connected to a RF generator for supplying energy to a wireless surgical device.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, as shown in FIG. 1A, a source or active electrode 2 delivers radio frequency energy from the electrosurgical generator 20 to the tissue and a return electrode 2 carries the current back to the generator. In monopolar electrosurgery, the source electrode is typically part of the surgical instrument held by the surgeon and applied to the tissue to be treated. A patient return electrode is placed on the patient P remotely from the active electrode to carry the current back to the generator.

In bipolar electrosurgery, as shown in FIG. 1B, one of the electrodes of the hand-held instrument functions as the active electrode 14 and the other as the return electrode 16. The return electrode is placed in close proximity to the active electrode such that an electrical circuit is formed between the two electrodes (e.g., electrosurgical forceps 10). In this manner, the applied electrical current is limited to the body tissue positioned immediately adjacent to the electrodes. When the electrodes are sufficiently separated from one another, the electrical circuit is open and thus inadvertent contact with body tissue with either of the separated electrodes does not cause current to flow.

Electrosurgical instruments have become widely used by surgeons in recent years. By and large, most electrosurgical instruments are hand-held instruments, e.g., an electrosurgical pencil, which transfer radio-frequency (RF) electrical or electrosurgical energy to a tissue site. As used herein the term "electrosurgical pencil" is intended to include instruments which have a handpiece that is attached to an active electrode and which is used to cauterize, coagulate and/or cut tissue. Typically, the electrosurgical pencil may be operated by a handswitch or a foot switch. The active electrode is an electrically conducting element that is usually elongated and may be in the form of a thin flat blade with a pointed or rounded distal end. Alternatively, the active electrode may include an elongated narrow cylindrical needle that is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

Some electrosurgical procedures utilize electrosurgical forceps that use both mechanical clamping action and electrical energy to affect hemostasis by heating tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are typically inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas. Such endoscopic instruments may use monopolar forceps, bipolar forceps or a combination monopolar/bipolar forceps.

During surgery, a surgeon generally uses more than one instrument and switching instruments can cause the cables to entangle. Entangled cables limit the movement of the instrument and cause delays in performing the surgery. Additionally, the cables used to connect the surgical devices have substantial weight, where the substantial weight of the cable can cause strain on the surgeon during long surgeries.

SUMMARY

In accordance with the present disclosure, a system and method for powering a wireless electrosurgical device using a powered glove. The powered glove includes at least a conductive pad on a finger and a thumb. The glove is connected to a generator and supplies power to the wireless electrosurgical device when at least two conductive pads touch conductive buttons on the wireless device. The user selects the operating mode by selecting different combination of conductive buttons and/or switches on the wireless device. The generator senses a voltage drop across a circuit within the electrosurgical device to determine the operating mode. The generator then supplies the RF energy based on the selected operating mode via the glove to the wireless device.

According to an embodiment of the present disclosure, a method for operating a wireless hand held electrosurgical device includes attaching a glove to a generator with a cable. The glove includes at least one embedded wire connected to a conductive pad on a finger tip, thumb, or palm of the glove. The method further includes selecting a contact button or contact trigger on a wireless electrosurgical device to select an operating mode using the conductive pad on the glove and notifying the generator of the selected mode using a message signal sent through the glove to the generator. Additionally, the method includes supplying an RF electrical signal through the glove to a treatment portion of the wireless device based on the selected mode.

According to another embodiment of the present disclosure, a glove system for powering a surgical device includes a wireless electrosurgical device, a glove, and a generator. The wireless electrosurgical device includes at least a first contact switch for setting an operating mode and a second contact switch. The glove includes at least two conductive pads, and at least one conductive pad is configured to select the operating mode. The generator is configured to supply RF energy based on the selected operating mode to the wireless electrosurgical device via the glove when the at least two conductive pads are touching the first and second contact switches.

According to another embodiment of the present disclosure, a method of using a glove to power an electrosurgical instrument includes touching a contact switch on a wireless bipolar device with a conductive pad on the power glove to select a first operating mode for the wireless bipolar device and determining a voltage drop across a first circuit within the wireless bipolar device to determine the first operating mode. Further, the method includes supplying RF energy in the first selected mode through the power glove to the wireless bipolar device to perforin a first electrosurgical procedure and touching a contact switch on a wireless monopolar device with the conductive pad on the power glove to select a second operating mode for the monopolar device. Additionally, the method includes determining a voltage drop across a second circuit within the wireless monopolar device to determine the second operating mode, and supplying RF energy in the second selected mode through the power glove to the wireless to monopolar device to perform a second electrosurgical procedure.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
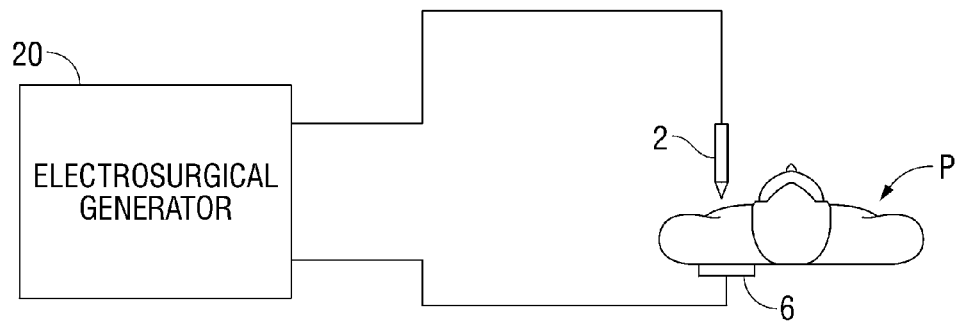
FIGS. 1A-1B are schematic diagrams of electrosurgical systems.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the term "RF" generally refers to electromagnetic waves having a lower frequency than microwaves.

Figure 2:
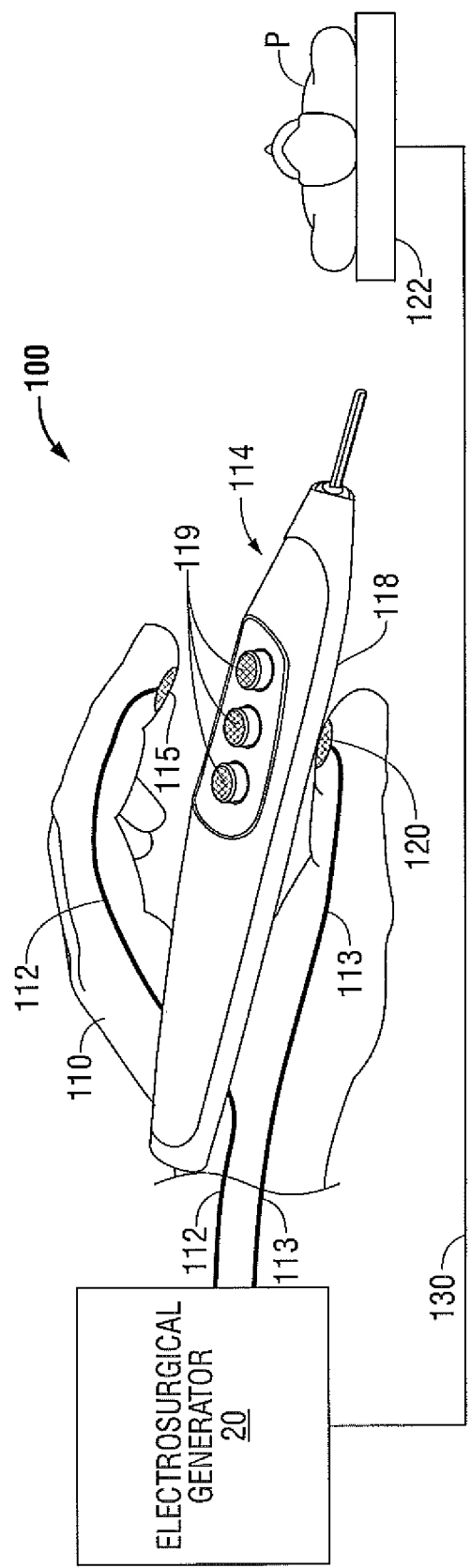
FIG. 2 is a perspective view of an electrosurgical pencil and generator in accordance with an embodiment of the present disclosure.

FIG. 2 shows a power glove system constructed in accordance with an embodiment of the present disclosure is shown generally as 100. A power glove 110 is connected to an electrosurgical generator 20 through at least two cables 112, 113. The power glove 110 includes a conductive pad 115 on the index finger and a second conductive pad 120 on the thumb. In alternative embodiments, the power glove could include conductive pads on other fingers or the palm (See for example FIG. 4). The conductive pads 115, 120 are connected to the generator 20 through connections 112, 113 respectively. The conductive pad 115 connects with at least one contact switch 119 on a wireless electrosurgical pencil 114. The contact switch 119 may be one, two, or three buttons and contacting/depressing certain combinations may activate different modes of operation. Cable 112 may transmit a selected mode to the generator 20 and/or supply RF energy to the wireless electrosurgical pencil 114. Additionally, cable 113 may transmit a selected mode to the generator 20 and/or supply RF energy to the wireless electrosurgical pencil 114. As a safety measure, activation of RF energy to the wireless electrosurgical pencil 114 may only be sent when at least two conductive pads 115, 120 interconnect with two separate contact switches 119, 118.

During an electrosurgical procedure the wireless electrosurgical pencil 114 is placed within the surgical site of patient P. RF energy is supplied to the wireless electrosurgical pencil 114 via cable 112 and/or 113. The RF energy is transferred through the patient P to a return pad 122. The return pad 122 is connected to the generator 20 via cable 130.

Figure 3:
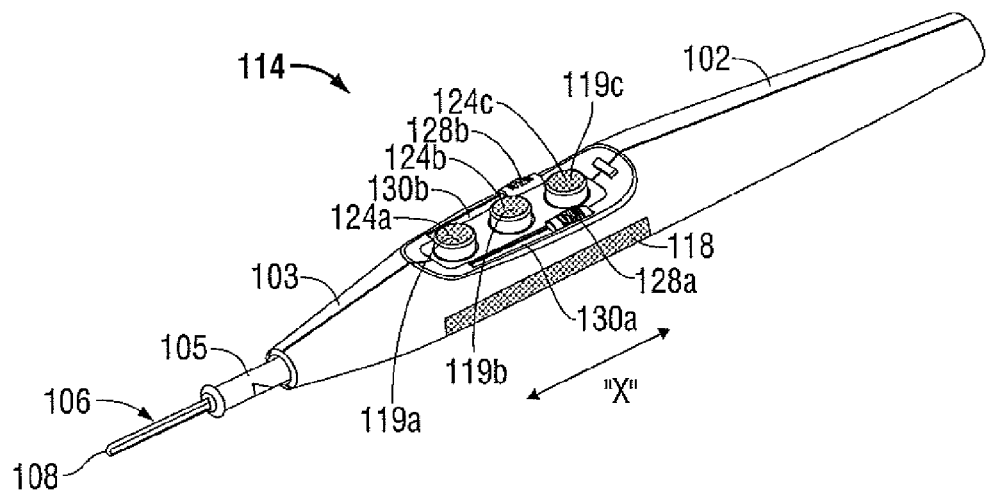
FIG. 3 is a perspective view of a wireless electrosurgical pencil in accordance with an embodiment of the present disclosure.

FIG. 3 shows an electrosurgical pencil 114 constructed in accordance with an embodiment of the present disclosure. Electrosurgical pencil 114 includes an elongated housing 102 configured and adapted to support a blade receptacle 105 at a distal end 103 thereof which, in turn, receives a replaceable electrocautery end effector 106 in the form of a loop and/or blade therein. Electrocautery blade 106 is understood to include a planar blade, a loop, a needle and the like. A distal end portion 108 of blade 106 extends distally from receptacle 104 while a proximal end portion of blade 106 is retained within distal end 103 of housing 102. Electrocautery blade 106 may be fabricated from a conductive type material, such as, for example, stainless steel, or is coated with an electrically conductive material.

For the purposes herein, the terms "switch" or "switches" includes electrical actuators, mechanical actuators, electro-mechanical actuators (rotatable actuators, pivotable actuators, toggle-like actuators, buttons, etc.) or optical actuators.

Electrosurgical pencil 114 includes at least one activation switch, e.g., three activation switches 124a-124c, each of which are supported on an outer surface of housing 102. Each activation switch 124a-124c includes a contact switch 119a-119c, which, in turn, controls the transmission of RF electrical energy supplied from the generator 20 to electrosurgical blade 106 via power glove 110. More particularly, contact switches 119a-119c are electrically coupled to the generator 20 via cable 112 (FIG. 2) and are configured to send an instruction selecting an operational mode to the generator 20. Alternatively, the generator 20 can determine a voltage drop across a circuit within the electrosurgical pencil (See FIGS. 7-9). The operational mode can include cut, ablate, coagulate, or seal depending on the surgical instrument being employed. The generator 20 then supplies RF energy to end effector 106 based on the selected operational mode via cable 112 and/or 113.

Electrosurgical pencil 114 may further include one or more intensity controllers 128a and/or 128b, each of which are slidingly supported in guide channels 130a, 130b, respectively, which are formed in outer surface of housing 102. Each intensity controller 128a and 128b is a slide-like potentiometer. Each intensity controller 128a and 128b and respective guide channel 130a and 130b may be provided with a series of cooperating discreet or detented positions defining a series of positions to allow easy selection of output intensity from a minimum amount to a maximum amount. The series of cooperating discreet or detented positions also provide the surgeon with a degree of tactile feedback. One of the series of positions for intensity controllers 128a, 128b may be an "off" position (i.e., no level of electrical or RF energy is being transmitted) as an added safety feature.

Intensity controllers 128a and 128b are configured and adapted to adjust one of the power parameters (e.g., RF energy field, voltage, power and/or current intensity) and/or the power verses impedance curve shape to affect the perceived output intensity.

Figure 4:
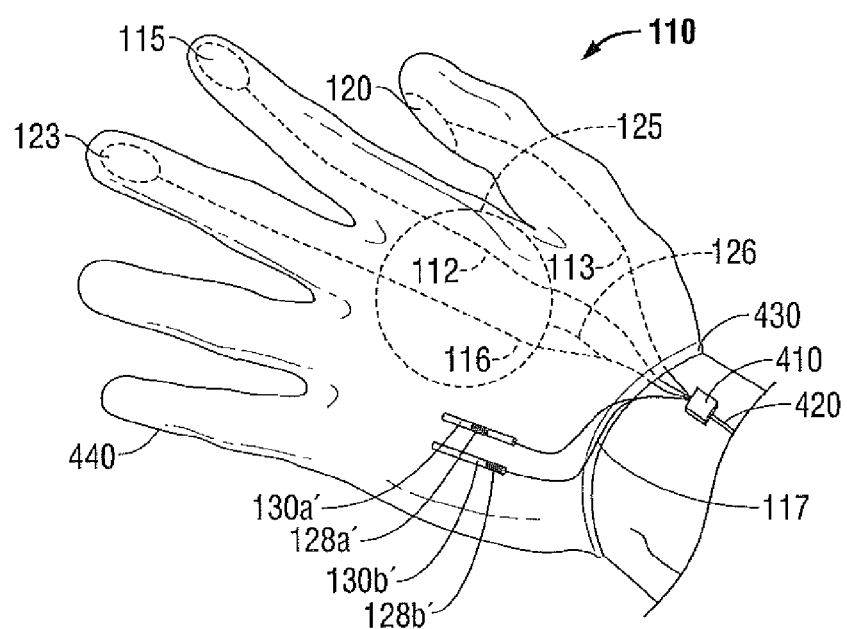
FIG. 4 is a perspective view of a power glove in accordance with an embodiment of the present disclosure.

FIG. 4 discloses a perspective view of a power glove 110. The power glove 110 may include conductive pads on or more fingers 115, 123, the thumb 120, and/or the palm 125. The conductive pads 115, 123, 120, 125 allow RF energy to flow from the generator 20 to the wireless electrosurgical device 114, 510 (see FIG. 5). Also, the electrical conductive pads 115, 123, 120, 125 allow information, such as operational mode or intensity information to be transferred to the generator 20 from the wireless electrosurgical device 114, 510. Any of the conductive pads 115, 123, 120, 125 may also function as a return pad and receive RF energy from a bipolar wireless electrosurgical device 510 to send RF energy back to the generator 20. The conductive pads may be made from copper, copper tungsten, gold, platinum, silver graphite, nickel, tin, or other specialty electrically conductive material.

The conductive pads 115, 123, 120, 125 are connected to cables 112, 116, 113, 126, respectively. The cables 112, 116, 113, 126 extend out from the cuff 430 of the power glove 110. The cables 112, 116, 113, 126 may extend a distance sufficient to reach the generator 20, which may include having cables 112, 116, 113, 126 extend over the surgeon's shoulder and still allow the surgeon sufficient movement (See FIG. 6). The cables 112, 116, 113, 126 may extend to a clip 410 that connects the cables 112, 116, 113, 126 to a connection cable 420. The connection cable 420 is of sufficient length to allow the surgeon sufficient movement. The connection cable 420 and clip 410 allow for separate replacement of connection cable 420 and the power glove 110, which may be important depending on the surgical procedure requirements for new sterile equipment versus reused sterile equipment. Alternatively, connection cable 420 may be embedded within sterile gown 60 (See FIG. 6) and replaceable after each use.

The conductive pads 115, 123, 120, 125, cables 112, 116, 113, 126, and/or connection cable 420 may be supplied separately from the glove 440. Supplying the glove 440 separate from the conductive pads 115, 123, 120, 125, cables 112, 116, 113, 126, and/or connection cable 420 allows the glove 440 to be for single use and the conductive pads 115, 123, 120, 125, cables 112, 116, 113, 126, and/or connection cable 420 for multiple uses. The conductive pads 115, 123, 120, 125, cables 112, 116, 113, 126, and/or connection cable 420 may be sterilized as an entire unit or sterilized in pieces if clip 410 disconnects cables 112, 116, 113, 126 from connection cable 420.

The power glove 110 may also include one or more intensity controllers 128a' and/or 128b', each of which are slidingly supported in guide channels 130a', 130b', respectively, which are formed in outer surface of glove 440. The one or more intensity controllers 128a' and/or 128b' may replace or operate with the one or more intensity controllers 128a and/or 128b on the wireless surgical device 114. Each intensity controller 128a' and 128b' is a slide-like potentiometer. Each intensity controller 128a' and 128b' and respective guide channel 130a' and 130b' may be provided with a series of cooperating discreet or detented positions defining a series of positions to allow easy selection of output intensity from a minimum amount to a maximum amount. The series of cooperating discreet or detented positions also provide the surgeon with a degree of tactile feedback. One of the series of positions for intensity controllers 128a', 128b' may be an "off" position (i.e., no level of electrical or RF energy is being transmitted) as an added safety feature.

Intensity controllers 128a' and 128b' are configured and adapted to adjust one of the power parameters (e.g., RF energy field, voltage, power and/or current intensity) and/or the power verses impedance curve shape to affect the perceived output intensity.

Figure 5:
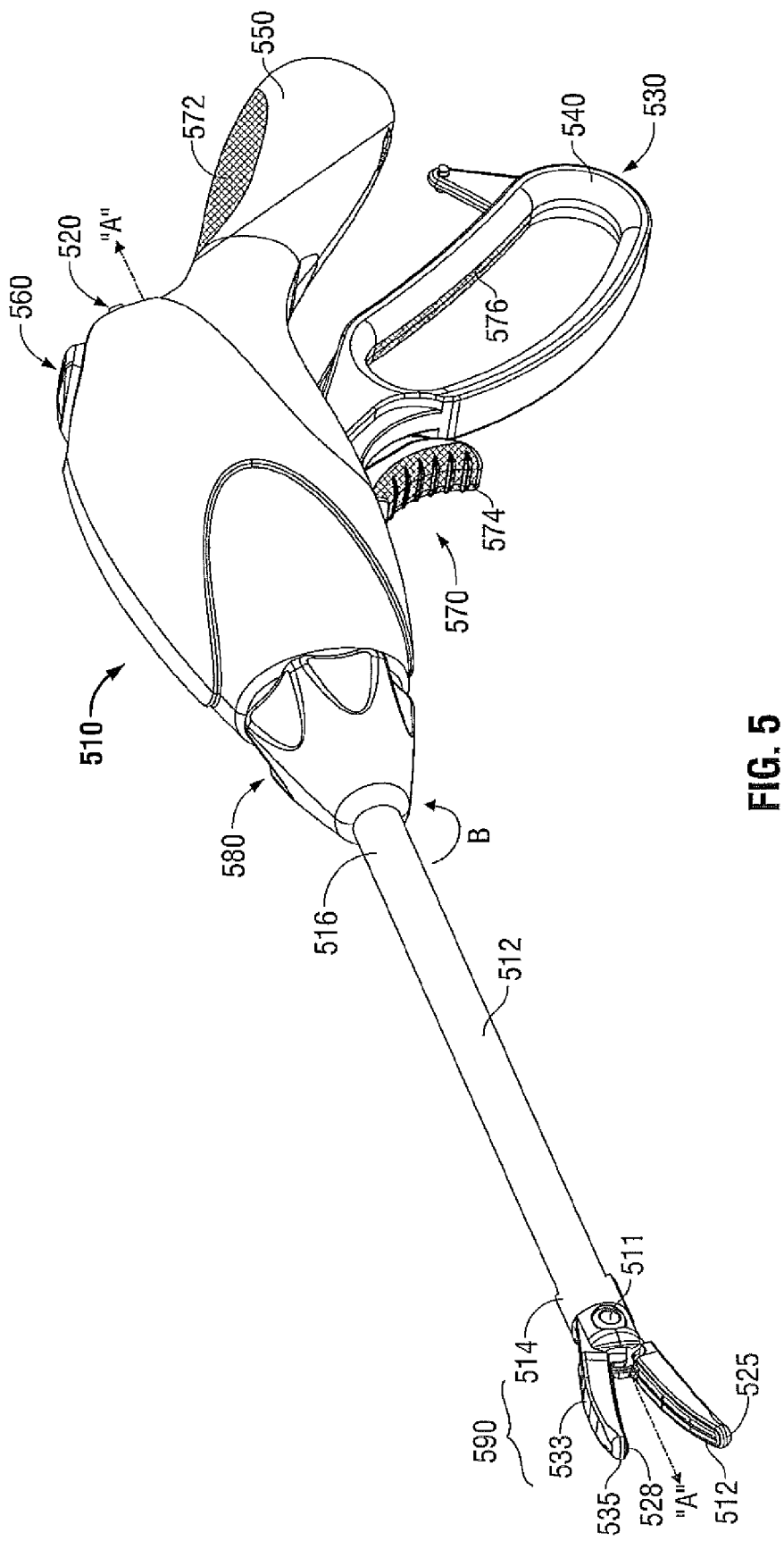
FIG. 5 is a perspective view of a wireless endoscopic forceps according to the present disclosure.

With reference to FIG. 5 an illustrative embodiment of a wireless electrosurgical apparatus, e.g., a bipolar forceps 510 (forceps 510) is shown. Forceps 510 is wirelessly connected to electrosurgical generator 20 via power glove 110 for performing an electrosurgical procedure. The electrosurgical procedure may include sealing, cutting, cauterizing, coagulating, desiccating, and fulgurating tissue all of which may employ RF energy. The electrosurgical generator 20 may be configured for monopolar and/or bipolar modes of operation and may include or be in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse to the forceps 510.

Forceps 510 is shown configured for use with various electrosurgical procedures and generally includes a housing 520, a rotating assembly 580 and a trigger assembly 570. For a more detailed description of the rotating assembly 580, trigger assembly 570, reference is made to commonly-owned U.S. patent application Ser. No. 11/595,194 filed on Nov. 9, 2006, now U.S. Patent Publication No. 2007/0173814. The trigger assembly 570 includes a contact switch 574 that when connected with a conductive pad 115, 123, 120, 125 of the power glove 110 allows RF energy to be transferred to the forceps 510 and/or to transfer an operational mode and/or intensity setting the generator 20. Additionally, the housing 520 may include a contact switch 560 that allows a conductive pad 120 within the thumb of the glove to transfer RF energy from the generator 20 to the bipolar device.

With continued reference to FIG. 5, forceps 510 includes a shaft 512 that has a distal end 514 configured to mechanically engage an end effector assembly 590 operably associated with the forceps 510 and a proximal end 516 that mechanically engages the housing 520.

Handle assembly 530 includes a fixed handle 550 and movable handle 540. In one particular embodiment, fixed handle 550 is integrally associated with housing 520 and handle 540 is movable relative to fixed handle 550 for effecting movement of one or more components, e.g., a drive wire 533, operably associated with a drive assembly (not shown) via one or more suitable mechanical interfaces, e.g., a linkage interface, gear interface, or combination thereof. Additionally, handle assembly 530 can be used to pivot jaw members 525 and 535 of end effector 590 around pivot pin 511.

Drive assembly (not shown) is in operative communication with handle assembly 530 for imparting movement of one or both of a pair of jaw members 525, 535 of end effector assembly 590. The drive assembly facilitates closing the jaw members 525 and 535 relative to one another. Drive wire 533 is configured such that proximal movement thereof causes the movable jaw member, e.g., jaw member 535, and operative components associated therewith, e.g., a seal plate 528, to "flex" or "bend" inwardly substantially across a length thereof toward the non-movable jaw member, e.g., jaw member 525. With this purpose in mind, drive rod or wire 533 may be made from any suitable material and is proportioned to translate within the shaft 512. In the illustrated embodiments, drive wire 533 extends through the shaft 512 past the distal end 514.

The handle assembly 530 may include a contact switch 576 on moveable handle 540. Contact switch 576 may allow RF energy to be supplied to the forceps 510 and/or to send an operational mode and/or intensity setting to the generator 20 when connected with any conductive pad 115, 123, 120, 125 of the power glove 110. Additionally, the handle assembly 530 may include a return contact switch 572 on fixed handle 570. The return contact switch 572 allows RF energy to be returned to the generator 20 via a palm conductive pad 125.

Figure 6:
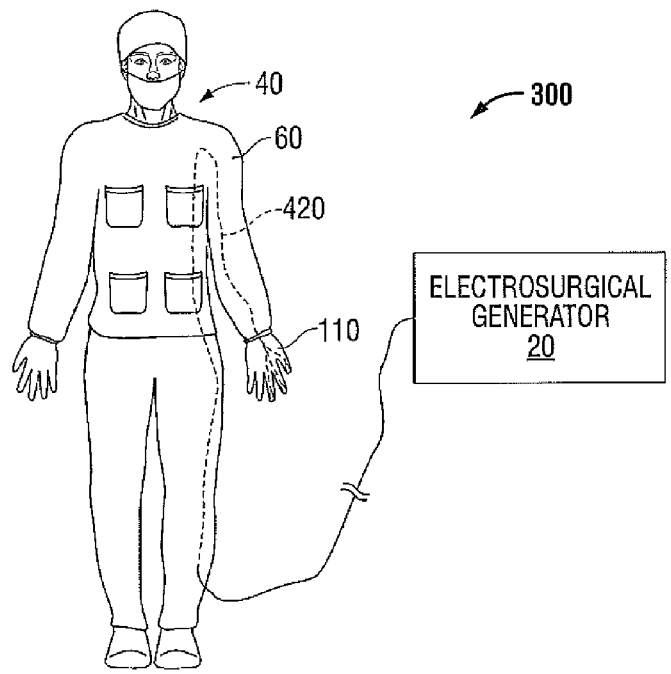
FIG. 6 is a perspective view of a surgeon, power glove and a generator in accordance with an embodiment of the present disclosure.

FIG. 6 shows a power glove system and a surgeon in accordance with an embodiment of the present disclosure is shown generally as 300. A surgeon 40 wears a sterile gown 60 that allows a connection cable 420 to be placed over, under, or within the sterile gown 60. The connection cable 420 may instead be cables 112, 113, 116, 117, and/or 126. The connection cable 420 may be removably connected to power glove 110 or permanently attached to the glove 440 and/or connect pads 115, 123, 120, and/or 125. The connection cable 420 connects to the generator 20 without severely limiting the surgeon's 40 movement. The surgeon 40 is able to move between tools without worrying about moving cables as the only cable is over the surgeon's 40 shoulder.

Figure 7:
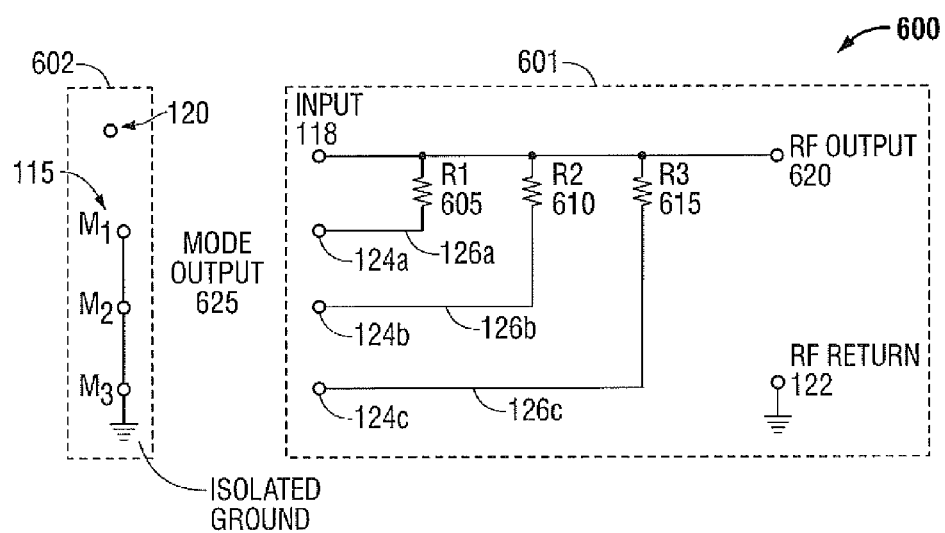
FIG. 7 is a schematic of a circuit in accordance with an embodiment of the present disclosure.

FIG. 7 is a schematic diagram representation 600 of the electrosurgical instrument 114 (alternatively electrosurgical instrument 510 may be used) and glove 110. Schematic circuit 600 is divided into two circuit portions 601, 602. Circuit portion 601 is part of the electrosurgical device 114 and includes three resistors 605, 610, 615. Each resistor 605, 610, 615 is electrically connected to one of the three activation switch contacts 124a-124c. For example, resistor R1 605 is electrically connected to activation switch contact 124a. Resistor R2 610 is electrically connected to activation switch 124b and resistor R3 615 is electrically connected to activation switch 124c. Each activation switch contact 124a-124c is operatively connected to a respective switch 126a-126c which, in turn, controls the transmission of RF electrical energy supplied from the generator 20 to end effector 106.

Figure 1B:
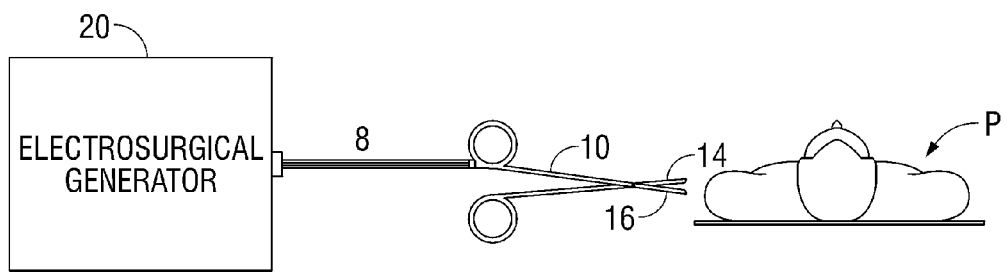

Circuit portion 602 is part of the glove 110. The conductive pad 115 attached to the indexed finger makes contact with at least one of the activation switch contacts 124a-124c. The thumb conductive pad 120 contacts with the input switch pad 118. In operation, for example, when the first and second conductive pads 115, 120 make contact with a respective activation switch contact 124a and input switch pad 118, a test voltage travels from the RF output 620 to mode output 625 so that the generator 110 detects resistor R1 605. Additionally, the test voltage travels from RF output 620 through patient P (FIG. 2) to RF return pad 122 and to the generator 20 via transmission line 130 (FIG. 1) in accordance with resistor R1 605. In another scenario if the first conductive pad 115 makes contact with the activation switch contact 124b, the generator senses R2 610 is electrically connected and generates electrosurgical energy to return through the return pad 122.

Figure 8:
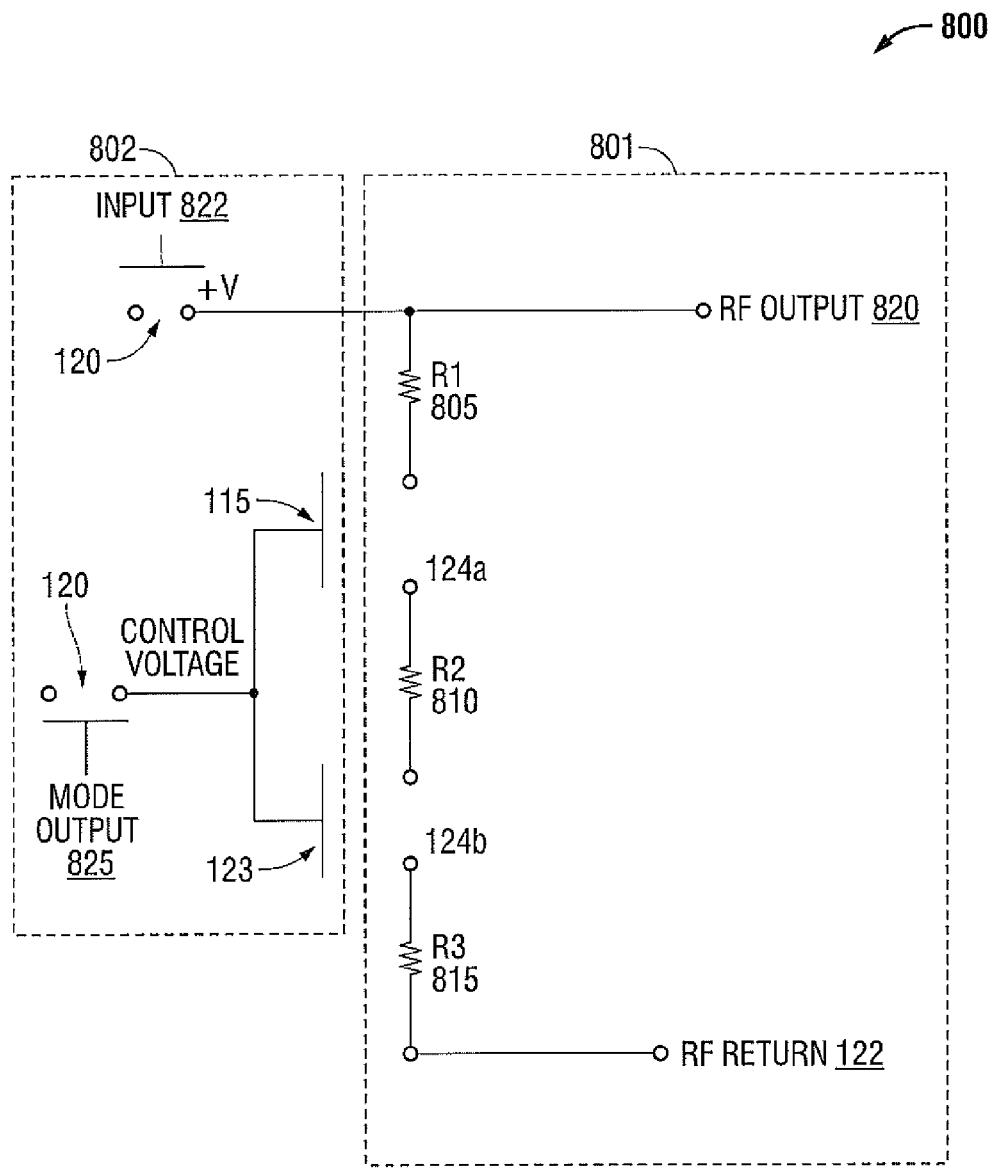
FIG. 8 is a schematic of a circuit in accordance with an embodiment of the present disclosure.

FIG. 8 is another embodiment of a schematic representation of the glove 110 and the activation switch contacts 124a-124b of the electrosurgical device 114. Schematic 800 envisions a third conductive pad 123 that is on any other finger of the glove 110 to activate a low and high electrosurgical energy. Schematic circuit 800 is divided into two circuit portions 801 and 802. Circuit portion 801 is part of the electrosurgical device 114 or 510. The circuit portion 801 includes three resistors 805, 810, 815 connected in series with activation switch contacts 124a-124b. Circuit portion 802 is part of the glove 110. Circuit portion 802 includes first and second conductive pads 115, 120. Circuit portion 802 also include a third conductive pad 123 that is on the middle finger of the instrument/glove 10. The third conductive pad 123 provides a higher electrosurgical energy as explained below. In operation, the surgeon uses the second conductive pad 120 that is the thumb to make contact with either the output 825 or the input 822. The surgeon then uses the first conductive pad 115 that is the indexed finger to make contact with activation switch contact 124a, a lower setting is activated and a lower electrosurgical energy is sent to the RF output 820. While maintaining the first and second conductive pads 115, 120, the surgeon may further use the third conductive pad 123 that is the middle finger to make contact with activation switch pad 124b. To this end, a higher power setting is sensed by the electrosurgical generator 20 and a higher power electrosurgical energy is sent to the RF output 820.

Figure 9:
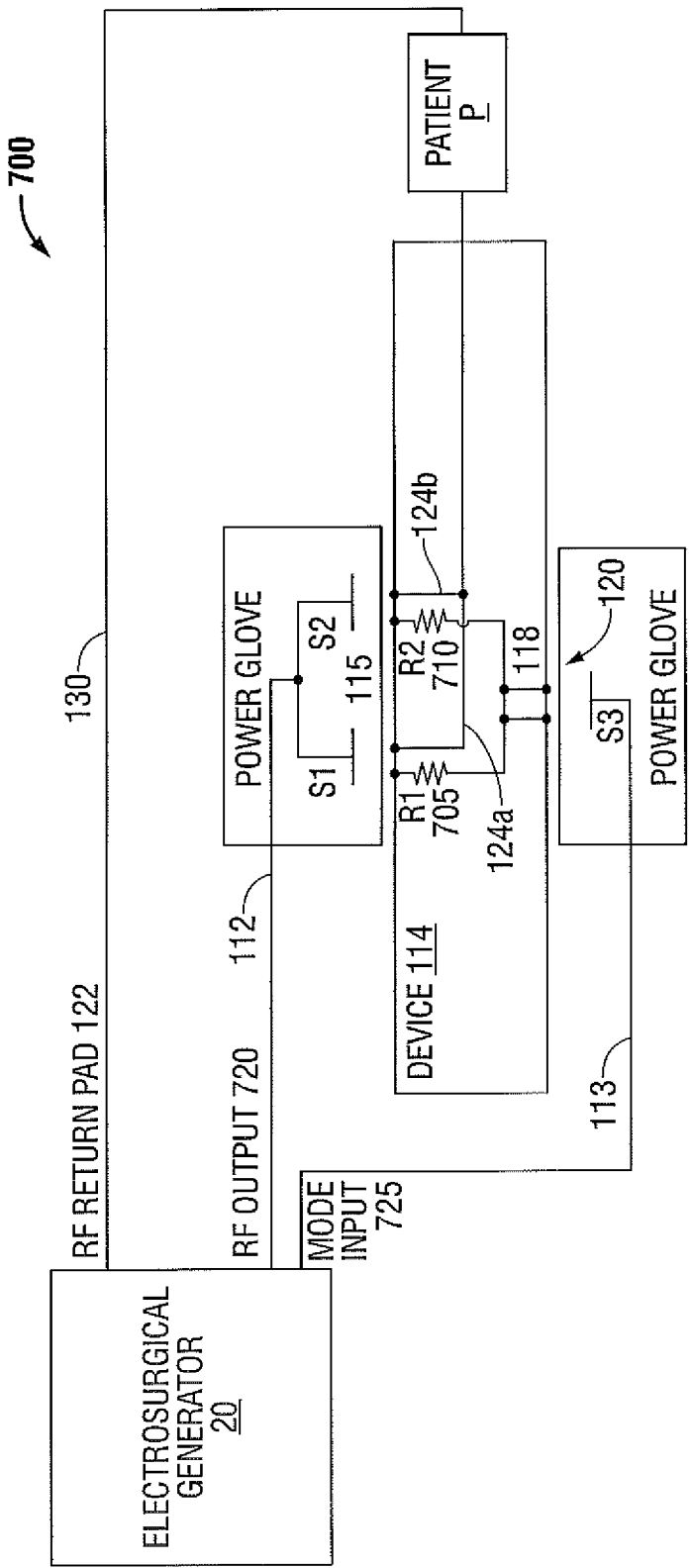
FIG. 9 is a schematic of a circuit in accordance with an embodiment of the present disclosure.

FIG. 9 is another embodiment of a schematic representation of the electrosurgical instrument/glove 10 and the activation switch contacts 124a-124b of the electrosurgical device 114. Schematic 700 is similar to schematic 600 with the exception that there are two switch contacts 124a, 124b instead of three switch contacts 124a-124c of FIG. 5. The first conductive pad 115 that is the index finger makes contact with anyone of the activation switch contacts 124a, 124b. The second conductive pad 120 that is the thumb finger makes contact with the input switch pad 118. In operation, for example, when the first and second conductive pads 115, 120 make contact with a respective activation switch contact 124a and input switch pad 118, a test voltage travels from the RF output 720 to mode input 725 so that the generator 20 detects the resistor R1 705 and applies electrosurgical energy to the RF output 720 to be return through RF return pad 122 via transmission line 130 in accordance with R1 705. In another scenario if the first conductive pad 115 makes contact with the activation switch contact 124b, the generator senses R2 710 is electrically connected and generate electrosurgical energy to return through the return pad 122.

Figure 10:
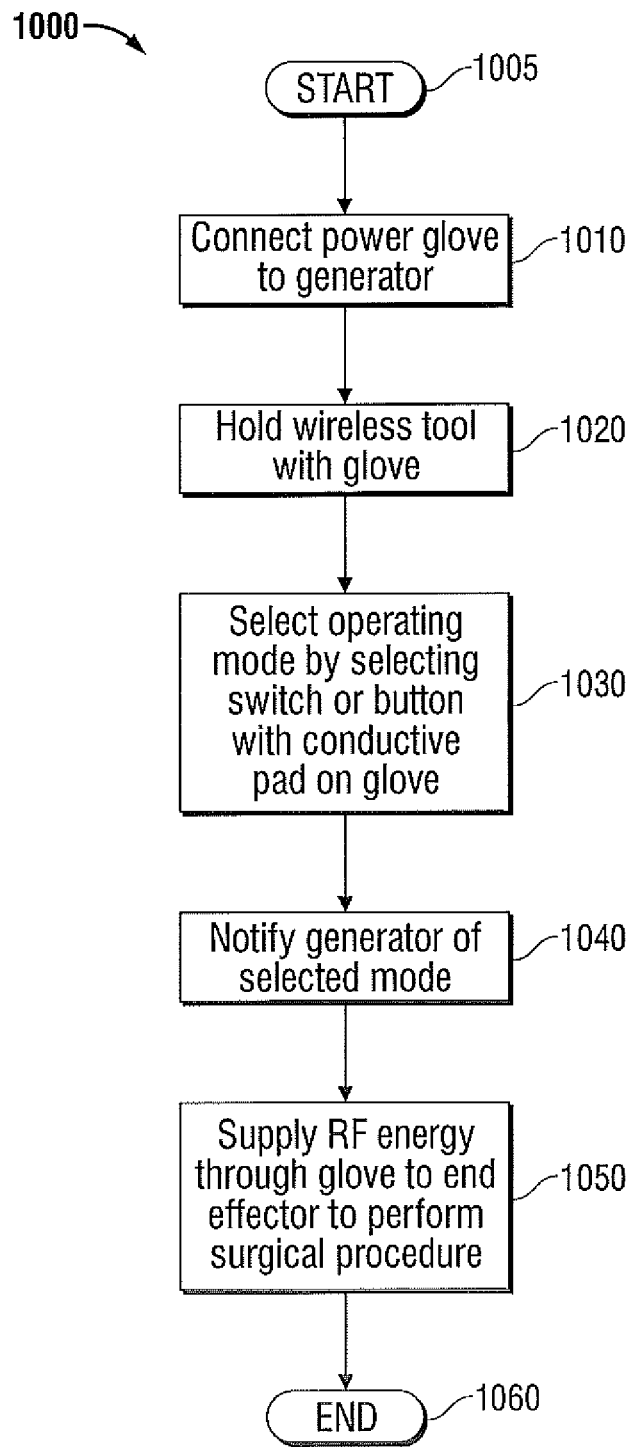
FIG. 10 is a flow chart of using a power glove and a wireless RF system according to the present disclosure.

FIG. 10 is a flow diagram of process 1000 for operating a wireless device, such as 114 or 510, using a power glove 110. The process 1000 starts at step 1005, a surgeon 40 or user connects a power glove 110 to a generator 20 at step 1010. A surgeon 40 holds a wireless device 114, 510 with the power glove 110 at step 1020. Next at step 1030, the surgeon 40 selects an operating mode by for example selecting at least one switch 124a-124c or button on device 114 by touching conductive pad 115 with at least one contact switch 119a-

119c. The generator 20 then is notified of the selected mode at step 1040. The generator 20 may be notified by sending a test pulse and measuring the resistance drop and/or output voltage. Alternatively, a controller module (not shown) within an electrosurgical device 114 or 510 can send information over cable 112 and/or 113 to the generator 20. Based on the selected mode, the generator 20 supplies the RF energy to the end effector 106, 590 via the power glove 110 to perform the electrosurgical procedure at step 1050. The procedure 1000 ends at step 1060 when the surgical procedure is complete. Also, the procedure 1000 may end as a safety precaution when the surgeon 40 removes one conductive pad 115, 120 from the wireless device 114, 510.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. The glove system for powering a wireless electrosurgical device, comprising:
   a return pad configured to couple to a patient;
   the wireless electrosurgical device including a first contact switch for setting an operating mode of the wireless electrosurgical device and a second contact switch, the operating mode being selected from the group consisting of cutting, ablating, coagulating, and sealing, the wireless electrosurgical device being a monopolar device;
   a glove including a first conductive pad configured to select the operating mode of the wireless electrosurgical device and a second conductive pad; and
   a generator configured to supply radio-frequency (RF) energy to the wireless electrosurgical device through the glove in response to the first contact switch selecting the operating mode of the wireless electrosurgical device by contacting the first contact switch with the first conductive pad and by contacting the second contact switch with the second conductive pad.

2. The glove system of claim 1, wherein the generator is configured to:
   sense a voltage drop across a circuit within the wireless electrosurgical device; and
   supply the RF energy based on the voltage drop.

3. The system of claim 1, further comprising:
   a detachable cable configured to attach the glove to the generator to deliver the RF energy from the generator to the wireless electrosurgical device through the glove.

4. The system of claim 1, wherein the glove is detachably connected to the first and second conductive pads.

5. The system of claim 4, wherein the glove is a single use disposable glove and the first and second conductive pads are configured for multiple uses.

6. The system of claim 1, further comprising a first mechanical activation switch for activating the RF energy, the first contact switch being disposed on the first mechanical activation switch.

7. The glove system for powering a wireless electrosurgical device, comprising:
   the wireless electrosurgical device including a first contact switch for setting an operating mode of the wireless electrosurgical device and a second contact switch, the operating mode being selected from the group consisting of cutting, ablating, coagulating, and sealing, the wireless electrosurgical device being a bipolar device;
   a glove including a first conductive pad configured to select the operating mode of the wireless electrosurgical device, a second conductive pad, and a palm conductive pad;
   a generator configured to supply radio-frequency (RF) energy to the wireless electrosurgical device through the glove in response to the first contact switch selecting the operating mode of the wireless electrosurgical device by contacting the first contact switch with the first conductive pad and by contacting the second contact switch with the second conductive pad; and
   a return pad contact that interconnects with the palm conductive pad on the glove to return the RF energy to the generator.

8. The system of claim 7, further comprising:
   a detachable cable configured to attach the glove to the generator to provide for a return path for the RF energy from the wireless electrosurgical device to the generator through the glove.

9. The system of claim 7, further comprising:
   a cable connecting the glove to the generator to deliver the RF energy from the generator to the wireless electrosurgical device through the glove and return the RF energy from the wireless electrosurgical device to the generator through the glove.

10. The glove system for powering a wireless electrosurgical device, comprising:
    a generator;
    a glove including a first conductive pad and a second conductive pad; and
    the wireless electrosurgical device including a circuit, a first contact switch and a second contact switch, the first contact switch configured to transmit a signal in response to a voltage drop across the circuit to the generator indicative of an operating mode of the wireless electrosurgical device when the first conductive pad of the glove contacts the first contact switch, wherein the generator is configured to supply radio-frequency (RF) energy to the wireless electrosurgical device through the glove in response to the second conductive pad contacting the second contact switch and the voltage drop.

11. The system of claim 10, wherein the operating mode is selected from the group consisting of cutting, ablating, coagulating, and sealing.

12. The system of claim 10, wherein the wireless electrosurgical device is a monopolar device and the glove system includes a return pad that is configured to couple to a patient.

13. The system of claim 12, further comprising:
    a detachable cable configured to attach the glove to the generator to deliver the RF energy from the generator to the wireless electrosurgical device through the glove.

14. The system of claim 10, wherein the wireless electrosurgical device is a bipolar device and includes a return pad contact that interconnects with a palm conductive pad on the glove to return the RF energy to the generator.

15. The system of claim 14, further comprising:
    a detachable cable configured to attach the glove to the generator to provide for a return path for the RF energy from the wireless electrosurgical device to the generator through the glove.

16. The system of claim 10, wherein the glove is detachably connected to the first and second conductive pads.

17. The system of claim 16, wherein the glove is a single use disposable glove and the first and second conductive pads are configured for multiple uses.

18. The system of claim 10, further comprising a first mechanical activation switch for activating the RF energy, the first contact switch being disposed on the first mechanical activation switch.

* * * * *